(12) United States Patent
Mueller et al.

(10) Patent No.: US 8,057,536 B2
(45) Date of Patent: Nov. 15, 2011

(54) IMPLANT HAVING A SURFACE-PROXIMAL MAGNESIUM-CONTAINING DIFFUSION LAYER AND ASSOCIATED PRODUCTION METHOD

(75) Inventors: Heinz Mueller, Erlangen (DE); Peter Uggowitzer, Ottenbach (CH); Joerg Loeffler, Schneisingen (CH)

(73) Assignee: Biotronik VI Patent AG, Baar (CH)

( * ) Notice: Subject to any disclaimer, the term of this patent is extended or adjusted under 35 U.S.C. 154(b) by 81 days.

(21) Appl. No.: 12/138,873

(22) Filed: Jun. 13, 2008

(65) Prior Publication Data
US 2008/0312736 A1 Dec. 18, 2008

(30) Foreign Application Priority Data

Jun. 15, 2007 (DE) .......................... 10 2007 023 284

(51) Int. Cl.
*A61F 2/06* (2006.01)
(52) U.S. Cl. ...................................... 623/1.46; 623/1.44
(58) Field of Classification Search ................. 623/1.15, 623/1.42–1.46; 264/602
See application file for complete search history.

(56) References Cited

U.S. PATENT DOCUMENTS

| | | | |
|---|---|---|---|
| 2005/0146086 A1* | 7/2005 | Pope et al. | 264/602 |
| 2007/0135908 A1* | 6/2007 | Zhao | 623/1.46 |
| 2008/0015578 A1* | 1/2008 | Erickson et al. | 606/61 |

FOREIGN PATENT DOCUMENTS

| | | |
|---|---|---|
| DE | 69906441 T2 | 4/2004 |
| DE | 10361941 A1 | 7/2005 |
| DE | 102005003188 A1 | 7/2006 |
| DE | 102006011348 A1 | 9/2007 |
| DE | 102006013115 A1 | 9/2007 |
| WO | 9927147 A2 | 6/1999 |

OTHER PUBLICATIONS

Search Report for German Patent Application No. 10 2007 023 284.7; Dec. 13, 2007.

* cited by examiner

*Primary Examiner* — Thomas J Sweet
*Assistant Examiner* — Matthew Schall
(74) *Attorney, Agent, or Firm* — Jason A. Bernstein; Barnes & Thornburg LLP

(57) ABSTRACT

An implant comprising an implant material forming a base made of one or more metallic elements; a diffusion layer covering the base made of at least one of the metallic elements of the implant material and at least magnesium; and, optionally, a metal layer covering the diffusion layer made of magnesium or a biocorrodible magnesium alloy.

11 Claims, 1 Drawing Sheet

IMPLANT HAVING A SURFACE-PROXIMAL MAGNESIUM-CONTAINING DIFFUSION LAYER AND ASSOCIATED PRODUCTION METHOD

PRIORITY CLAIM

This patent application claims priority to German Patent Application No. 10 2007 023 284.7, filed Jun. 15, 2007, the disclosure of which is incorporated herein by reference in its entirety.

FIELD

The present disclosure relates to an implant having a surface-proximal magnesium-containing diffusion layer and a method for producing same.

BACKGROUND

An implant is generally understood as any medical device made of one or more materials which is intentionally introduced into the body and is either partially or entirely covered by an epithelial surface. Implants may be divided into temporary and permanent implants in regard to the usage time. Temporary implants remain in the body for a limited time. Permanent implants are intended to remain permanently in the body. Furthermore, implants may be differentiated into prostheses and artificial organs. For purposes of the present disclosure, a prosthesis is a medical device which replaces limbs, organs, or tissue of the body, while an artificial organ is understood as a medical device which partially or entirely replaces the function of a bodily organ. For example, implants such as orthopedic or osteosynthetic implants, cardiac pacemakers and defibrillators, and vascular implants fall under the cited definitions.

An implant material is a nonliving material which is used for an application in medicine and interacts with biological systems. A basic requirement for the use of a material as an implant material, which is in contact with the bodily environment when used as intended, is its bodily compatibility (biocompatibility). For purposes of the present disclosure, biocompatibility is understood as the capability of a material to cause an appropriate tissue reaction in a specific application. This includes an adaptation of the chemical, physical, biological, and morphological surface properties of an implant to the receiving tissue with the object of a clinically desirable interaction. The biocompatibility of the implant material is also a function of the time curve of the reaction of the biosystem in which the implant material is implanted. Thus, relatively short-term irritations and inflammations occur which may result in tissue changes. Toxicity, allergies, or even cancer formation are the moderate to long-term results of a lack of biocompatibility.

Biological systems react differently to foreign bodies as a function of the properties of the material or component. The implant materials may be divided into bioactive, bioinert, and degradable/resorbable materials in accordance with the reaction of the biosystem.

For purposes of the present disclosure, only metallic implant materials are of interest, whose application is in osteosynthesis, joint replacement, dental surgery, and vascular surgery, for example. Biocompatible metals and metal alloys or permanent implants comprise rustproof steels (e.g., 316L), cobalt-based alloys (e.g., CoCrMo cast alloys, CoCrMo forged alloys, CoCrWNi forged alloys, and CoCrNiMo forged alloys), pure titanium and titanium alloys (e.g., cp titanium, TiAl6V4, or TiAl6Nb7), and gold alloys. In the field of biocorrodible implants, the use of magnesium or pure iron as well as biocorrodible base alloys of elements magnesium, iron, zinc, molybdenum, and tungsten are desirable.

A biological reaction to metallic elements is a function of the concentration, action time, and type of the supply. The presence of an implant material frequently results in inflammation reactions, whose triggers may be mechanical irritations, chemical materials, but also metabolic products. The inflammation reaction is typically accompanied by the immigration of neutrophilic granulocytes and monocytes through the vascular walls, the immigration of lymphocyte effector cells with formation of specific antibodies against the inflammation stimulus, the activation of the complementary system with release of complementary factors, which act as mediators, and finally the activation of blood coagulation. An immunological reaction is usually closely connected to the inflammation reaction and may result in sensitization and allergy formation. Known metallic allergens comprise, for example, nickel, chromium, and cobalt, which are also used as alloy components in many surgical implants.

In addition to its biocompatibility, the implant material must, of course, also always fulfill its functional tasks, namely, for example, at least temporarily ensuring the mechanical integrity of the implant and possibly shielding an implant interior in relation to the surrounding material. Because of this, frequently only compromises between all of the requirements to be fulfilled may be implemented on the material in the material selection.

Furthermore, it is known that a higher degree of biocompatibility may be achieved if metallic implant materials are provided with coatings made of especially tissue-compatible materials. These materials are usually of an organic or synthetic-polymer nature and are partially of natural origin. In spite of the progress achieved, there is still a high demand for at least alternative approaches. Thus, for example, the problem frequently arises that the coatings to be applied only adhere inadequately, in particular, in regard to the conditions existing during the implantation.

Furthermore, in manifold medical implants, the most solid and/or secure anchoring possible of the implant on the implantation location is desired. Fundamentally, especially in metallic permanent implants, the problem arises that an implant may not be integrated permanently in the meaning of biological ingrowth into the cell composite. This is usually expressed in the formation of a layer similar to connective tissue around the implant. This layer similar to connective tissue prevents the direct contact of the cells of the surrounding tissue with the implants; the implant is only still anchored by a form fit, but not by biological adhesion, by the cells in this case.

In the case of permanent implants made of titanium and titanium materials, direct colonization of the implant surface with vital cells is frequently observed, but in many cases the layer similar to connective tissue described here also occurs. In addition, an increasing tendency toward loosening and the formation of a layer similar to connective tissue is also frequently observed with progressing implantation time in titanium implants. In rare cases, bioincompatible to cytotoxic reactions also occur in titanium implants at the interface between implant and tissue, especially in the event of longer implantation times.

These reactions are even more significantly pronounced in the case of other implant materials, such as CoCr alloys or implant steels.

Special textures of the implant surface, which make colonization with cells easier and are to encourage the formation of contact points between cell and implant surface, also only inadequately solve the problem. Functional surfaces which are to suppress the formation of a layer similar to connective tissue by special coatings are still predominantly in the research stage; there are not yet reliable findings about the long-term suitability of these layers, which are frequently monomolecular.

If the experimentally available implants up to this point, made of the so-called biologically degradable materials, are also taken into consideration in this observation, biological incompatibilities up to necrosis of the tissue are also found here, especially if an accumulation of the degradation products of such metals is in contact with tissue. Such results have been found, for example, in the evaluation of zinc and zinc-based alloys as implant materials for vascular implants and are to be expected upon the use of degradable implants made of iron, iron alloys, tungsten, and other metals fundamentally degradable in the body, because the body identifies the compounds formed as foreign bodies and a foreign body reaction occurs. Such a reaction typically also results in activation of the immune system connected with a local inflammation. These impairments also result in a slowed healing procedure, connected with a delayed colonization with cells, the formation of layers similar to connective tissue, and a delayed healing procedure.

The surface of orthopedic implants made of the titanium alloy TiAl6V4 may be modified by ion beam implantation using magnesium ions in such a manner that the colonization by human osteoblasts is made easier (Zreiqat et al.; "The effect of surface chemistry modification of titanium alloy on signaling pathways in human osteoblasts"; Biomaterials; 2005; pp. 7579-7586). The ion implantation results in an enrichment of magnesium to a content of approximately 10 atomic-% to a depth of approximately 60 nm of the material. The entry depth of magnesium is a function of the energy of the incident ions, i.e., enrichment of the magnesium occurs in specific surface-proximal layers of the material depending on the energy profile. Conversion of the implant surface, which still contains or comprises titanium dioxide in the event of titanium and titanium alloys, does not occur.

SUMMARY

The present disclosure describes several exemplary embodiments of the present invention.

One aspect of the present disclosure provides an implant, comprising (i) an implant material forming a base made of one or more metallic elements; (ii) a diffusion layer covering the base made of at least one of the metallic elements of the implant material and at least magnesium; and (iii) optionally, a metal layer covering the diffusion layer made of magnesium or a biocorrodible magnesium alloy.

Another aspect of the present disclosure provides a method for surface modification of an implant, comprising (i) providing an untreated implant having an implant material forming the base made of one or more metallic elements; (ii) contacting the surface of the base using metallic magnesium or a biocorrodible magnesium alloy; and (iii) simultaneously with or following step (ii), thermally treating the implant at least in the area of the contact surface with formation of a diffusion layer covering the base made of at least one of the metallic elements of the implant material and at least magnesium.

In summary, there is, therefore, still a high demand for making possible better integration of a metallic implant in its biological environment. This comprises both the option of better colonization of the implant surface and the avoidance of the formation of layers similar to connective tissue, and also the better anchoring of an implant at the implantation location resulting therefrom. Of course, an improvement of the biocompatibility in general is desirable. In the case of biocorrodible metallic implant materials, the desire is to achieve more rapid colonization with cells.

An implant according to the present disclosure having (i) an implant material made of one or more metallic elements forming a base; (ii) a diffusion layer, covering the base, made of at least one of the metallic elements of the implant material and at least magnesium; and (iii) optionally, a metal layer, covering the diffusion layer, made of magnesium or a biocorrodible magnesium alloy overcomes or alleviates one or more of the disadvantages of the prior art described. The implant accordingly has a multilayered implant surface, which comprises a permanent or biocorrodible metallic implant material forming a base, and a diffusion layer, covering the base, made of one or more of the elements of the metallic implant material and at least magnesium. The diffusion layer may in turn be covered by a metal layer made of magnesium or a biocorrodible magnesium alloy.

The present disclosure is based on the finding that implants made of a permanent or biocorrodible metallic implant material having the diffusion layer according to the present disclosure are particularly advantageous. These implants display improved anchoring of the implant at the implantation location, a high degree of biocompatibility, improved colonization of the implant surface, and avoid the formation of layers similar to connective tissue. The metallic implant material is only used as the base on which the diffusion layer according to the present disclosure is applied. This diffusion layer is generated using a suitable processing method by depositing magnesium or a biocorrodible magnesium alloy on the base and simultaneously or subsequently reacting a surface-proximal part of the base made of the metallic implant material with at least parts of this deposition. In other words, the applied magnesium and/or the biocorrodible magnesium alloy forms the diffusion layer together with a surface-proximal part of the metallic implant material. The diffusion layer is formed in the course of the production method by diffusion procedures at the phase boundary between the two metallic layers. The alloy system of the diffusion layer which forms is a function of many factors, in particular, the temperature and treatment time during the production method, the composition of the base, and the composition of the magnesium-containing material used to prepare the diffusion layer. The resulting diffusion layer does not necessarily have to contain all elements of the base and/or of the magnesium alloy possibly used for the production; however, at least one metallic element of the base and magnesium are present.

Such a diffusion layer has a very high adhesive capability on the base, so that damage of the texture in the course of implantation may be largely avoided even in the event of high mechanical strain, for example.

A special advantage of the diffusion layer, however, is also that the components of the magnesium-containing alloy are subject to a special degradation process upon contact with physiological media or when they are implanted in vivo. According to initial findings of the applicant, there is no dissolving of the metal in the actual meaning, but rather a conversion process. After completed conversion, the organism forms a biological phase, which essentially comprises calcium, oxygen, phosphorus, and carbon, at the location at which the magnesium was originally located. The magnesium itself is completely dissolved and removed by the specific transport systems available in the body. A more precise mechanism of the process is not yet explained, however, the active conversion process described in the body has been shown by the applicant at various points in the bodies of experimental animals.

Implants which comprise a biocorrodible magnesium alloy form a new interface in the physiological environment through the conversion process described. In all experiments of biocompatibility and hemocompatibility up to this point, implants of this type have achieved above-average results. The conversion process begins immediately with the implantation, so that the modification of the implant surface according to the present disclosure is particularly suitable for orthopedic, osteosynthetic, or vascular implants. Further assays on explants have additionally shown that the interaction of the implant with its physiological environment during the conversion process is a so-called bioactive behavior of these materials, i.e., a stimulus for new formation of a biological phase or a biological tissue originates from the implant itself.

If such an implant is introduced into its physiological environment, the conversion reaction results in the new formation of a physiological phase described above. The reaction only converts the very thin external diffusion layer in the case of permanent implant materials, however, and comes to rest as soon as it reaches an area at which the concentration of the actual implant material, which is stable under physiological conditions, is high enough. In this way, a new composite made of the actual implant material and the biological system arises in situ and in vivo, in which the biologically formed phase passes as a type of gradient layer into the base material, which leads one to expect especially good anchoring of the implant.

For purposes of the present disclosure, alloys and elements in which a degradation/conversion occurs in the physiological environment, so that the part of the implant comprising the material is entirely or at least predominantly no longer present, are referred to as biocorrodible.

A concentration of magnesium in the diffusion layer preferably decreases from an exterior side of the implant toward the base. A special feature in such a coating in combination with a permanent implant material is that the body itself controls the depth to which it converts this coating of the implant, which in turn takes into consideration the various implantation locations and the physiological conditions present there, such as pH value and possible enrichment with specific ions, in particular.

Such an implant surface made of base and covering diffusion layer, which is capable of forming a biologically formed adhesion mediating layer, may be implemented in principle for all currently used permanent or biocorrodible metallic implant materials because, for example, through suitable thermal treatments, corresponding diffusion layers (or also interdiffusion layers) may be produced using all base materials relevant up to this point in medical technology. Preferably, (a) the metallic implant material is selected from the group consisting of the elements titanium, nickel, iron, cobalt, niobium, zinc, tungsten, molybdenum, and tantalum, or (b) the metallic implant material is a base alloy in which one of the elements selected from the group consisting of titanium, nickel, iron, cobalt, niobium, zinc, tungsten, molybdenum, and tantalum represents a main component. The main component is the alloy component whose weight proportion of the alloy is highest. A proportion of the main component is preferably more than 50 wt.-%, in particular, more than 70 wt.-%. For purposes of the present disclosure, alloys of this type are referred to as base alloys of the particular elements.

The metallic implant material is especially preferably titanium or a titanium alloy, such as CP titanium, TiAl6V4, TiAl6Nb7, or Nitinol. On one hand, titanium has a certain solubility for magnesium and, on the other hand, no intermetallic phases form in the system titanium/magnesium which avoids possible mechanical stress of the material composite by embrittlement. Furthermore, a very homogeneous setting of the concentration gradients in the diffusion layer is to be expected by appropriate setting of the process parameters during the production of the diffusion layer and due to the lack of intermetallic phases. Titanium and titanium alloys are typically covered by a layer made of titanium dioxide which is a few nanometers thick, but which significantly influences the reactivity of the material and surface properties. This oxide layer is reduced by the method explained in greater detail below for surface modification, i.e., for preparing the diffusion layer. Such a reductive conversion is only possible using magnesium and calcium. Any other element would not result in formation of a diffusion layer because of the oxide layer which obstructs diffusion.

Furthermore, the metallic implant material may preferably also be niobium, tantalum, a niobium alloy, or a tantalum alloy. The cited elements and their alloys also do not form brittle intermetallic phases.

Furthermore, it is preferable if the implant material comprises pure iron, a biocorrodible iron alloy, a biocorrodible tungsten alloy, a biocorrodible zinc alloy, or a biocorrodible molybdenum alloy.

According to a further exemplary embodiment which may also be implemented in connection with the above-mentioned exemplary embodiments, the diffusion layer contains pores. In the course of the metallographic analysis of experiments on an implant having a titanium base and a magnesium coating, it was established that the formation of microporosity occurs in the diffusion layer. A surface topography of this type on implants is desirable in the orthopedic field, for example, for the ingrowth of bone cells. The causes of the microporosity are not yet definitively explained. The differing diffusion of titanium and magnesium is suspected to cause the phenomenon (Kirkendall effect). The Kirkendall effect is that, at a sufficiently high temperature, with two solid phases pressing against one another, the volume of one phase decreases while the volume of the other phase increases. Characteristic holes also often arise near the phase boundary in the phase which decreases its volume, the so-called Kirkendall holes.

The pores preferably have an average pore size of 10 nm to 10 μm. In this case, (a) an average pore size of 10 nm to 1 μm and (b) an average pore size of 1 μm to 10 μm are especially preferable. Variant (a) is distinguished in that the pore size is especially favorable for colonization by human osteoblasts. Variant (b) is particularly suitable for receiving active ingredients and releasing them when used as intended (drug eluting).

The diffusion layer preferably has a layer thickness in the range from 20 nm to 20 μm. If the implant material is titanium or a titanium alloy, the layer thickness is preferably in the range from 2 μm to 20 μm.

If a metal layer is provided, it preferably has a layer thickness in the range from 10 nm to 1 mm, in particular 10 nm to 300 μm. Above 1 mm layer thickness, the danger of an embolism by hydrogen development or damage of the tissue by gas accumulation is too high. Layer thicknesses below 300 μm are to be classified as harmless in regard to their hydrogen release in any application.

The metal layer preferably comprises a biocorrodible magnesium alloy. For purposes of the present disclosure, a magnesium alloy is a metallic structure whose main component is magnesium. The main component is the alloy component whose weight proportion of the alloy is highest. A proportion of the main component is preferably more than 50 wt.-%, in particular, more than 70 wt.-%. Preferably, the biocorrodible magnesium alloy contains yttrium and further rare earth metals, because an alloy of this type is distinguished on the basis of its physiochemical properties and high biocompatibility, in particular, also its degradation products. A magnesium alloy of the composition rare earth metals 5.2-9.9 wt.-%, yttrium 3.7-5.5 wt.-%, and the remainder<1 wt.-% is especially preferable, magnesium making up the proportion of the alloy to 100 wt.-%. This magnesium alloy has already confirmed its special suitability in clinical trials, i.e., it displays a high biocompatibility, favorable processing properties, good mechanical characteristics, and corrosion behavior adequate for the intended uses. For purposes of the present disclosure, the collective term "rare earth metals" includes scandium (21), yttrium (39), lanthanum (57) and the 14 elements following lanthanum (57), namely cerium (58), praseodymium (59), neodymium (60), promethium (61), samarium (62), europium (63), gadolinium (64), terbium (65), dysprosium (66), holmium (67), erbium (68), thulium (69), ytterbium (70) und lutetium (71). Furthermore, magnesium alloys which contain up to 6 wt.-% zinc are preferable. A magnesium alloy of the composition yttrium 0.5-10 wt.-%, zinc 0.5-6 wt.-%, calcium 0.05-1 wt.-%, manganese 0-0.5 wt.-%, silver 0-1 wt.-%, cerium 0-1 wt.-%, and zirconium 0-1 wt.-% or silicon 0-0.4 wt.-%, is especially preferable, the specifications in wt.-% relating to the alloy and magnesium and contaminants caused by production making up the residual proportion of the alloy remaining up to 100 wt.-%. Zinc appears to play a special role in bone formation, in particular, a specific effect on the proliferation of osteoblastic cells has been reported. After performing the method according to the present disclosure, zinc is a component of the diffusion layer and/or the metal layer.

The magnesium alloy is to be selected in its composition in such a way that it is biocorrodible. Artificial plasma, as has been previously described according to EN ISO 10993-15:2000 for biocorrosion assays (composition NaCl 6.8 g/l, CaCl2 0.2 g/l, KCl 0.4 g/l, MgSO4 0.1 g/l, NaHCO3 2.2 g/l, Na2HPO4 0.126 g/l, NaH2PO4 0.026 g/l), is used as a testing medium for testing the corrosion behavior of an alloy coming into consideration. For this purpose, a sample of the alloy to be assayed is stored in a closed sample container with a defined quantity of the testing medium at 37° C. At time intervals, tailored to the corrosion behavior to be expected, of a few hours up to multiple months, the sample is removed and examined for corrosion traces in a known way. The artificial plasma according to EN ISO 10993-15:2000 corresponds to a medium similar to blood and thus represents a possibility for simulating a physiological environment reproducibly in the meaning of the present disclosure.

The invention may be used in all implants which comprise permanent or biocorrodible metallic implant materials or which at least have components made of a permanent or biocorrodible metallic implant material which are in contact with the surrounding tissue after the implantation. The implant is especially preferably a vascular, orthopedic, or osteosynthetic implant.

A further feature of the present disclosures provides a method for producing the implant modified on the implant surface in the above-mentioned way. The method according to one exemplary embodiment of the present disclosure comprises the following steps:
 (i) providing an untreated implant having an implant material, forming a base, made of one or more metallic elements;
 (ii) contacting the surface of the base with metallic magnesium or a biocorrodible magnesium alloy; and
 (iii) simultaneously with or following step (ii), thermal treatment of the implant at least in area of the contact surface with formation of a diffusion layer, covering the base, made of at least one of the metallic elements of the implant material and at least magnesium.

The method according to this embodiment thus provides refining an implant having an implant surface made of a permanent or biocorrodible metallic implant material in that a diffusion layer made of parts of this implant material and magnesium and/or the biocorrodible magnesium alloy is generated.

The contacting in step (ii) may be performed via a CVD or a PVD method, a flame spraying method or an electrolysis method. A further preferred method is the galvanic coating of the implant surface with magnesium. The contacting is preferably performed, however, by immersion in a melt made of magnesium or a biocorrodible magnesium alloy. A temperature in the area to be treated is then preferably between melting temperature and melting temperature+300° C.

Step (iii) is preferably performed in such a manner that a concentration of magnesium in the resulting diffusion layer decreases from an exterior side of the implant toward the base. This diffusion layer then has a concentration gradient for magnesium, i.e., the atomic proportion/weight proportion of magnesium in the alloy forming the diffusion layer decreases toward the base. A layer thickness of the diffusion layer formed is a function, on one hand, of the quantity of the applied magnesium/the magnesium alloy and, on the other hand, of the extent of the reaction of the applied material with the metallic implant material in the surface-proximal area of the implant surface.

Step (iii) may preferably be performed such that pores arise in the diffusion layer. Furthermore, step (iii) may be performed such that the resulting diffusion layer is covered by a metal layer.

BRIEF DESCRIPTION OF THE DRAWINGS

Various aspects of the present disclosure are described hereinbelow with reference to the accompanying FIGURE.

DETAILED DESCRIPTION

Example 1

Figure 1:
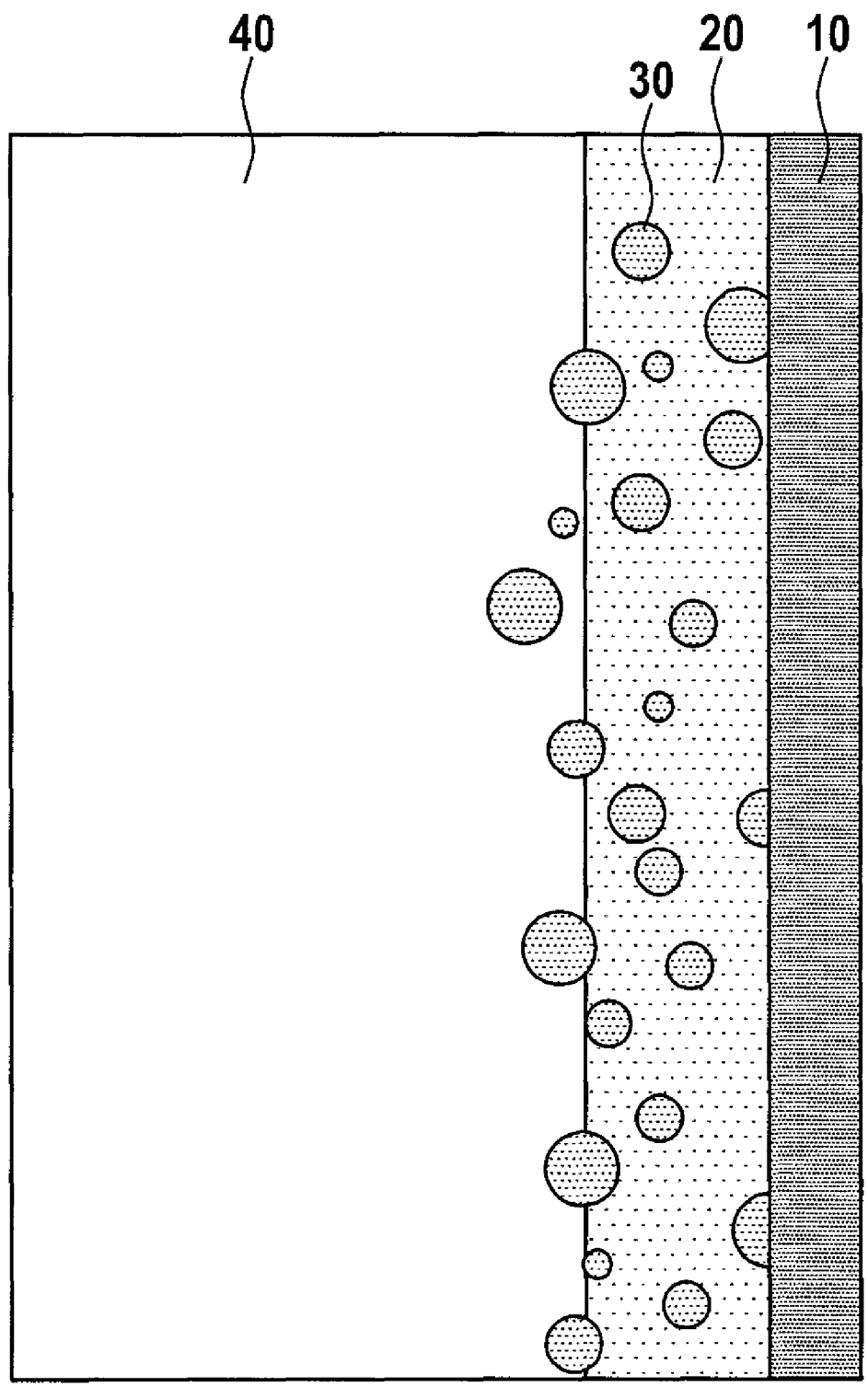
FIG. 1 shows a schematic sectional view through an implant having a diffusion layer according to one exemplary embodiment of the present disclosure.

A rod-shaped implant made of CP titanium was immersed in a melt made of pure magnesium of 750° C. in a vacuum melt furnace and held for 30 minutes therein. The implant was then drawn out of the melt and held just above the melt bath for 10 minutes. The melt metallurgy treatment resulted in the formation of an approximately 7-μm-thick diffusion layer.

The coating comprised an approximately 2-μm-thick magnesium layer 10 and an approximately 5-μm-thick diffusion layer 20 having decreasing magnesium content toward the interior of the titanium implant (base 40). Pores 30 resulted in the diffusion layer 20, having a pore size of 1-5 μm (cf. schematic sectional illustration of FIG. 1 prepared on the basis of a finish grinding).

In the system titanium/magnesium, the following structure of the diffusion layer 20 starting from the base 40 appears to be conclusive: a single-phase system made of titanium and magnesium exists up to a boundary of approximately 3 atomic-% magnesium (with gradual increase of the magnesium content). This is adjoined by an area having a dual-phase system, in which titanium and magnesium exist adjacent to one another, the magnesium proportion rising continuously.

Example 2

A magnesium alloy of the composition (in wt.-%) 2.0% Zn, 0.8% Y, and 0.25% Ca was melted at 750° C. in a crucible under protective atmosphere. A rod-shaped implant made of CP titanium was immersed in the melt bath and held for 60 minutes therein. The implant was then drawn out of the melt and cooled in normal atmosphere. This melt metallurgy treatment resulted in the formation of an approximately 9-μm-thick diffusion layer having decreasing magnesium content toward the interior of the titanium implant. Pores having a pore size of 1-5 μm resulted in the alloy layer.

What is claimed is:

1. An implant, comprising:
   (i) an implant material forming a base made of one or more metallic elements;
   (ii) a diffusion layer formed by a combination comprising at least one of the metallic elements of the implant material and magnesium, whereby the diffusion layer has a gradient whereby the concentration of magnesium in the diffusion layer decreases from the exterior of the diffusion layer toward the interior of the base; and
   (iii) a metallic layer covering the diffusion layer, the metallic layer comprising either magnesium or a biocorrodible magnesium alloy.

2. The implant of claim 1, wherein the diffusion layer contains pores.

3. The implant of claim 2, wherein the pores have an average pore size of 10 nm to 10 μm.

4. The implant of claim 3, wherein the pores have an average pore size of 10 nm to 1 μm.

5. The implant of claim 3, wherein the pores have an average pore size of 1 μm to 10 μm.

6. The implant of claim 1, wherein the diffusion layer has a layer thickness in the range from 20 nm to 20 μm.

7. The implant of claim 1, wherein the diffusion layer has a layer thickness in the range from 2 μm to 20 μm.

8. The implant of claim 1, wherein the metal layer has a layer thickness in the range from 10 nm to 1 mm.

9. The implant of claim 8, wherein the metal layer has a layer thickness in the range from 10 nm to 300 μm.

10. The implant of claim 1, wherein the diffusion layer or the metallic layer contain zinc.

11. The implant of claim 1, wherein implant material comprises titanium and the metallic material comprises magnesium, and wherein the diffusion layer comprises a single phase system comprising titanium and magnesium existing up to a boundary of approximately 3 atomic-% magnesium and having a gradual increase of magnesium content extending away from the base, and an area of a dual-phase system whereby titanium and magnesium exist adjacent to one another with the proportion of magnesium increasing away from the base.

* * * * *